(12) United States Patent
Li et al.

(10) Patent No.: US 8,361,355 B2
(45) Date of Patent: Jan. 29, 2013

(54) PREPARATION OF ANTIMICROBIAL CONTACT LENSES WITH REDUCED HAZE USING SWELLING AGENTS

(75) Inventors: Yongcheng Li, St. Augustine, FL (US); Stephen R. Beaton, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/010,117

(22) Filed: Jan. 20, 2011

(65) Prior Publication Data

US 2011/0111120 A1    May 12, 2011

Related U.S. Application Data

(63) Continuation of application No. 12/055,654, filed on Mar. 26, 2008, now abandoned.

(60) Provisional application No. 60/909,009, filed on Mar. 30, 2007.

(51) Int. Cl.
*B29D 11/00* (2006.01)
*B29C 44/08* (2006.01)

(52) U.S. Cl. .......................... 264/2.6; 264/343
(58) Field of Classification Search .................. 264/2.6, 264/343
See application file for complete search history.

(56) References Cited

U.S. PATENT DOCUMENTS

| | | | |
|---|---|---|---|
| 3,408,429 A | 10/1968 | Otto | |
| 3,660,545 A | 5/1972 | Otto | |
| 3,700,761 A * | 10/1972 | O'Driscoll et al. | 264/1.36 |
| 3,808,178 A | 4/1974 | Gaylord | |
| 4,046,706 A | 9/1977 | Krezanoski et al. | |
| 4,113,224 A | 9/1978 | Clark | |
| 4,120,570 A | 10/1978 | Gaylord | |
| 4,136,250 A | 1/1979 | Mueller | |
| 4,139,513 A | 2/1979 | Tanaka | |
| 4,139,692 A | 2/1979 | Tanaka | |
| 4,153,641 A | 5/1979 | Deichert | |
| 4,182,822 A | 1/1980 | Chang | |
| 4,189,546 A | 2/1980 | Deichert | |
| 4,197,266 A | 4/1980 | Clark | |
| 4,254,248 A | 3/1981 | Friends | |
| 4,259,467 A | 3/1981 | Keogh | |
| 4,260,725 A | 4/1981 | Keogh | |
| 4,261,875 A | 4/1981 | Le Boeuf | |
| 4,276,402 A | 6/1981 | Chromecek | |
| 4,327,203 A | 4/1982 | Deichert | |
| 4,341,889 A | 7/1982 | Deichert | |
| 4,343,927 A | 8/1982 | Chang | |
| 4,354,952 A | 10/1982 | Riedhammer et al. | |
| 4,355,147 A | 10/1982 | Deichert | |
| 4,450,264 A | 5/1984 | Cho | |
| 4,463,149 A | 7/1984 | Ellis | |
| 4,486,577 A | 12/1984 | Mueller | |
| 4,495,313 A | 1/1985 | Larsen | |
| 4,525,563 A | 6/1985 | Shibata | |
| 4,537,746 A | 8/1985 | Ogunbiyi et al. | |
| 4,543,398 A | 9/1985 | Bany | |
| 4,605,712 A | 8/1986 | Mueller | |
| 4,661,575 A | 4/1987 | Tom | |
| 4,680,336 A | 7/1987 | Larsen | |
| 4,703,097 A | 10/1987 | Wingler | |
| 4,711,943 A | 12/1987 | Harvey, III | |
| 4,837,289 A | 6/1989 | Mueller | |
| 4,871,785 A | 10/1989 | Froix | |
| 4,889,664 A | 12/1989 | Kindt Larsen | |
| 4,954,586 A | 9/1990 | Toyoshima | |
| 4,954,587 A | 9/1990 | Mueller | |
| 5,010,141 A | 4/1991 | Mueller | |
| 5,034,461 A | 7/1991 | Lai | |
| 5,039,459 A | 8/1991 | Kindt Larsen | |
| 5,057,578 A | 10/1991 | Spinelli | |
| 5,070,215 A | 12/1991 | Bambury | |
| 5,314,960 A | 5/1994 | Spinelli | |
| 5,336,797 A | 8/1994 | McGee | |
| 5,346,946 A | 9/1994 | Yokoyama | |
| 5,358,995 A | 10/1994 | Lai | |
| 5,371,147 A | 12/1994 | Spinelli | |
| 5,387,632 A | 2/1995 | Lai | |
| 5,451,617 A | 9/1995 | Lai | |
| 5,486,579 A | 1/1996 | Lai | |
| 5,710,302 A | 1/1998 | Kunzler et al. | |
| 5,714,557 A | 2/1998 | Kunzler | |
| 5,760,100 A | 6/1998 | Nicolson et al. | |
| 5,776,999 A | 7/1998 | Nicolson et al. | |
| 5,789,461 A | 8/1998 | Nicolson et al. | |
| 5,807,944 A | 9/1998 | Hirt | |
| 5,820,918 A | 10/1998 | Ronan | |
| 5,849,811 A | 12/1998 | Nicolson et al. | |
| 5,908,906 A | 6/1999 | Kunzler | |
| 5,958,440 A | 9/1999 | Burrell | |
| 5,962,548 A | 10/1999 | Vanderlaan | |
| 5,965,631 A | 10/1999 | Nicolson | |
| 5,981,615 A | 11/1999 | Meijs | |
| 5,981,675 A | 11/1999 | Valint, Jr. | |

(Continued)

FOREIGN PATENT DOCUMENTS

| | | |
|---|---|---|
| EP | 406161 B1 | 2/1995 |
| JP | 2000-016905 | 1/2000 |
| WO | WO 94/21698 A1 | 9/1994 |
| WO | WO 99/27978 | 6/1999 |
| WO | WO 01/24837 A1 | 4/2001 |
| WO | WO 03/011351 | 2/2003 |
| WO | WO 03/022321 | 3/2003 |
| WO | WO 2004/047879 A | 6/2004 |
| WO | WO 2004/047879 A2 | 6/2004 |
| WO | WO 2006/012000 A | 2/2006 |
| WO | WO 2006/012000 A1 | 2/2006 |

OTHER PUBLICATIONS

U.S. Appl. No. 60/909,009, filed Mar. 30, 2007, Yongcheng.
U.S. Appl. No. 09/532,943, filed Mar. 22, 2000, Margiss.
Elimelech, M., Gregory J., Jia X., and Williams R., "Particle deposition and aggregation, measurement, modeling and simulation" pp. 54-55. Butterworth Heinemann, Oxford 1995.

(Continued)

*Primary Examiner* — Joseph Del Sole
*Assistant Examiner* — Ryan Ochylski

(57) ABSTRACT

This invention relates to antimicrobial lenses containing metals and methods for their production.

15 Claims, No Drawings

U.S. PATENT DOCUMENTS

| | | | |
|---|---|---|---|
| 5,998,498 | A | 12/1999 | Vanderlaan et al. |
| 6,020,445 | A | 2/2000 | Vanderlaan |
| 6,039,913 | A | 3/2000 | Hirt |
| 6,087,415 | A | 7/2000 | Vanderlaan et al. |
| 6,156,244 | A | 12/2000 | Muller et al. |
| 6,486,285 | B2 | 11/2002 | Fujita |
| 6,585,768 | B2 | 7/2003 | Hamano et al. |
| 7,112,652 | B2 | 9/2006 | Ford |
| 7,319,133 | B2 | 1/2008 | Brame et al. |
| 7,416,737 | B2 | 8/2008 | Alvarez-Carrigan et al. |
| 2001/0018464 | A1* | 8/2001 | Fujita .......................... 521/84.1 |
| 2004/0150788 | A1* | 8/2004 | Andersson et al. ....... 351/160 R |
| 2004/0151755 | A1* | 8/2004 | Rathore et al. ................ 424/429 |
| 2005/0008676 | A1 | 1/2005 | Qiu et al. |
| 2006/0100408 | A1 | 5/2006 | Powell et al. |
| 2008/0102100 | A1 | 5/2008 | Rathore |
| 2009/0051060 | A1 | 2/2009 | Li et al. |

OTHER PUBLICATIONS

James, T.H. "The theory of the photographic process", 4$^{th}$ Ed. Eastman Kodak Company, 1977.

* cited by examiner

PREPARATION OF ANTIMICROBIAL CONTACT LENSES WITH REDUCED HAZE USING SWELLING AGENTS

RELATED APPLICATION

This application is a continuation of U.S. patent application Ser. No. 12/055,654, filed Mar. 26, 2008, now abandoned which is a non-provisional filing of U.S. patent application Ser. No. 60/909,009, which was filed on Mar. 30, 2007, now abandoned.

FIELD OF THE INVENTION

This invention relates to methods of preparing antimicrobial lenses

BACKGROUND OF THE INVENTION

Contact lenses have been used commercially to improve vision since the 1950s. The first contact lenses were made of hard materials. They were used by a patient during waking hours and removed for cleaning. Current developments in the field gave rise to soft contact lenses, which may be worn continuously, for several days or more without removal for cleaning. Although many patients favor these lenses due to their increased comfort, these lenses can cause some adverse reactions to the user. The extended use of the lenses can encourage the buildup of bacteria or other microbes, particularly, *Pseudomonas aeruginosa*, on the surfaces of soft contact lenses. The build-up of bacteria and other microbes can cause adverse side effects such as contact lens acute red eye and the like. Although the problem of bacteria and other microbes is most often associated with the extended use of soft contact lenses, the build-up of bacteria and other microbes occurs for users of hard contact lens wearers as well.

U.S. Pat. No. 5,820,918 discloses medical devices made from a water absorbable polymer material with a medical compound having low solubility in aqueous solutions such as an antiseptic or radiopaque compound. However, the procedures disclosed in the examples yield opaque devices which are not suitable for ophthalmic devices such as contact lenses.

Therefore, there is a need to produce contact lenses that inhibit the growth of bacteria or other microbes and/or the adhesion of bacteria or other microbes on the surface of contact lenses. Further there is a need to produce contact lenses which do not promote the adhesion and/or growth of bacteria or other microbes on the surface of the contact lenses. Also there is a need to produce contact lenses that inhibit adverse responses related to the growth of bacteria or other microbes. Still further there is a need to produce the foregoing contact lenses in a manner that produces a lens of clarity suitable to permit a user to clearly see from said lenses. These needs are met by the following invention.

DETAILED DESCRIPTION OF THE INVENTION

This invention includes a method of preparing an antimicrobial lens comprising, a metal salt, wherein said method comprises the steps of
   (a) treating a cured lens, with a solution comprising a salt precursor and a swelling agent,
   (b) treating the lens of step (a) with solution comprising a swelling agent for an appropriate period of time, and
   (c) treating the lens of step (b) with a solution comprising a metal agent and a swelling agent.

As used herein, the term, "antimicrobial lens" means a lens that exhibits one or more of the following properties, the inhibition of the adhesion of bacteria or other microbes to the lenses, the inhibition of the growth of bacteria or other microbes on lenses, and the killing of bacteria or other microbes on the surface of lenses or in an area surrounding the lenses. For purposes of this invention, adhesion of bacteria or other microbes to lenses, the growth of bacteria or other microbes on lenses and the presence of bacteria or other microbes on the surface of lenses are collectively referred to as "microbial colonization." Preferably, the lenses of the invention exhibit a reduction of viable bacteria or other microbe of at least about 0.25 log, more preferably at least about 0.5 log, most preferably at least about 1.0 log ($\geqq$90% inhibition). Such bacteria or other microbes include but are not limited to those organisms found in the eye, particularly *Pseudomonas aeruginosa*, *Acanthamoeba* species, *Staphylococcus. aureus*, *Escherichia. coli*, *Staphylococcus epidermidis*, and *Serratia marcesens*.

As used herein the term "swelling agent" refers substances that increase the size of a lens. As defined hereinafter the lenses of the invention absorb water after they are cured. This absorbance of water gives a lens that has water equilibrated dimensions (i.e. diameter, water content). These dimensions are different depending upon the composition of the lens formulation. Swelling agents may be used on lenses after they are cured or after they have absorbed water and have reached their water equilibrated dimensions. Such agents increase the dimensions of the lens beyond that of its water equilibrated dimensions. It is preferred that the swelling agents of the invention be used to treat lenses that have absorbed water to their water equilibrated dimensions. Examples of swelling agents include but are not limited to extracting solvents as disclosed in U.S. Pat. No. 7,112,652, entitled "Solvents Useful in the Preparation of Polymers Containing Hydrophilic and Hydrophobic Monomers", which is hereby incorporated by reference. Particularly examples of swelling agents include but are not limited to aqueous isopropanol, aqueous propylene glycol, ethylene glycol-n-butyl ether, diethylene glycol-n-butyl ether, diethylene glycol methyl ether, ethylene glycol phenyl ether, propylene glycol methyl ether, dipropylene glycol methyl ether, tripropylene glycol methyl ether, propylene glycol methyl ether acetate, dipropylene glycol methyl ether acetate, propylene glycol-n-propyl ether, dipropylene glycol-n-propyl ether, tripropylene glycol-n-butyl ether, propylene glycol-n-butyl ether, dipropylene glycol-n-butyl ether, tripropylene glycol-n-butyl ether, tripropylene glycol-n-propyl ether, proplyene glycol phenyl ether, dipropylene glycol dimethyl ether, butyl acetate, dipropylene glycol methyl ether acetate, and diproplyeneglycol dimethyl ether. The preferred swelling agents are about 30% to about 70% aqueous isopropanol and about 30% to about 70% aqueous propylene glycol, where the particularly preferred swelling agent is about 30% to about 70% aqueous isopropanol, more preferably 50% aqueous isopropanol. It is preferred that the swelling agent does not increase the size of the lenses beyond the size of the lenses after step (a).

As use herein, the term "metal salt" means any molecule having the general formula $[M]_a[X]_b$ wherein X contains any negatively charged ion, a is $\geqq$1, b is $\geqq$1 and M is any positively charged metal selected from, but not limited to, the following $Al^{+3}$, $Co^{+2}$, $Co^{+3}$, $Ca^{+2}$, $Mg^{+2}$, $Ni^{+2}$, $Ti^{+2}$, $Ti^{+3}$, $Ti^{+4}$, $V^{+2}$, $V^{+3}$, $V^{+5}$, $Sr^{+2}$, $Fe^{+2}$, $Fe^{+3}$, $Au^{+2}$, $Au^{+3}$, $Au^{+1}$, $Pd^{+2}$, $Pd^{+4}$, $Pt^{+2}$, $Pt^{+4}$, $Cu^{+1}$, $Cu^{+2}$, $Mn^{+2}$, $Mn^{+3}$, $Mn^{+4}$, $Zn^{+2}$, and the like. Examples of X include but are not limited to $CO_3^{-2}$, $NO_3^{-1}$, $PO_4^{-3}$, $Cl^{-1}$, $I^{-1}$, $Br^{-1}$, $S^{-2}$, $O^{-2}$ and the like. Further X includes negatively charged ions containing $CO_3^{-2}$ $NO_3^{-1}$, $PO_4^{-3}$, $Cl^{-1}$, $I^{-1}$, $Br^{-1}$, $S^{-2}$, $O^{-2}$, and the like, such as $C_{1-5}alkylCO_2^{-1}$. As used herein the term metal salts does not include zeolites, disclosed in WO03/011351. This patent application is hereby incorporated by reference in its entirety. The preferred a is 1, 2, or 3. The preferred b is 1, 2, or 3. The preferred metals ions are $Mg^{+2}$, $Zn^{+2}$, $Cu^{+1}$, $Cu^{+2}$, $Au^{+2}$, $Au^{+3}$, $Au^{+1}$, $Pd^{+2}$, $Pd^{+4}$, $Pt^{+2}$, $Pt^{+4}$, $Ag^{+2}$, and $Ag^{+1}$. The particularly preferred metal ion is $Ag^{+1}$. Examples of suitable metal salts include but are not limited to manganese sulfide, zinc oxide, zinc sulfide, copper sulfide, and copper phosphate. Examples of silver salts include but are not limited to silver nitrate, silver sulfate, silver iodate, silver carbonate, silver phosphate, silver sulfide, silver chloride, silver bromide, silver iodide, and silver oxide. The preferred silver salts are silver iodide, silver chloride, and silver bromide. The lenses of the invention are ophthalmic lenses (a detailed description of these lenses follows) and the clarity of the lenses is of concern to users.

The amount of metal in the lenses is measured based upon the total weight of the lenses. When the metal is silver, the preferred amount of silver is about 0.00001 weight percent (0.1 ppm) to about 10.0 weight percent, preferably about 0.0001 weight percent (1 ppm) to about 1.0 weight percent, most preferably about 0.001 weight percent (10 ppm) to about 0.1 weight percent, based on the dry weight of the lens. With respect to adding metal salts, the molecular weight of the metal salts determines the conversion of weight percent of metal ion to metal salt. The preferred amount of silver salt is about 0.00003 weight percent (0.3 ppm) to about 30.0 weight percent, preferably about 0.0003 weight percent (3 ppm) to about 3.0 weight percent, most preferably about 0.003 weight percent (30 ppm) to about 0.3 weight percent, based on the dry weight of the lens.

The term "solution" refers to aqueous or organic compositions that dissolve salt precursors. The preferred solutions are aqueous. Solutions may contain buffered salts such as sodium borate/boric acid, excipients, surfactants, wetting agents and the like. The term "salt precursor" refers to any compound or composition that contains a cation that may be substituted with metal ions. The concentration of salt precursor in its solution is between about 0.00001 to about 10.0 weight percent, (0.1-100,000 ppm) more preferably about 0.0001 to about 1.0 weight percent, (1-10,000 ppm) most preferably about 0.001 to about 0.1 weight percent (10-1,000 ppm) based upon the total weight of the solution. Examples of salt precursors include but are not limited to inorganic molecules such as sodium chloride, sodium iodide, sodium bromide, sodium sulfide, lithium chloride, lithium iodide, lithium bromide, lithium sulfide, potassium bromide, potassium chloride, potassium sulfide, potassium iodide, rubidium iodide, rubidium bromide, rubidium chloride, rubidium sulfide, caesium iodide, caesium bromide, caesium chloride, caesium sulfide, francium iodide, francium bromide, francium chloride, francium sulfide, sodium tetrachloro argentate, and the like. Examples of organic molecules include but are not limited to tetra-alkyl ammonium lactate, tetra-alkyl ammonium sulfate, quaternary ammonium halides, such as tetra-alkyl ammonium chloride, bromide or iodide. The preferred salt precursor is selected from the group consisting of sodium chloride, sodium iodide, sodium bromide, lithium chloride, lithium sulfide, sodium sulfide, potassium iodide, potassium sulfide, potassium bromide, potassium chloride, and sodium tetrachloro argentite and the particularly preferred salt precursor is sodium iodide.

The term "metal agent" refers to any composition (including aqueous solutions) containing metal ions. Examples of such compositions include but are not limited to aqueous or organic solutions of silver nitrate, silver triflate, or silver acetate, silver sulfate, silver tetrafluoroborate, silver sulfate, zinc acetate, zinc sulfate, copper acetate, copper sulfate, and the like, where the concentration of metal agent in solution is about 1 µg/mL or greater. The preferred metal agent is aqueous silver nitrate, where the concentration of silver nitrate is the solution is about greater than or equal to 0.0001 to about 2 weight percent, more preferably about greater than 0.001 to about 0.1 weight percent based on the total weight of the solution. The term "treating" refers to any method of contacting solutions containing any combination of swelling agent, metal agent, or salt precursor with the lens wherein the preferred method is immersing the lens in such solutions. Treating can include heating the lens in such solutions, but, preferred treatments are carried out at ambient temperatures and below. The time of this treatment can last anywhere from about 10 seconds to about 24 hours, preferably from about 30 seconds to about 60 minutes. With respect to step (a) is also preferred that treating is conducted at ambient temperature followed by cooler temperatures.

As used herein, the term "lens" refers to an ophthalmic device that resides in or on the eye. These devices can provide optical correction, wound care, drug delivery, diagnostic functionality, cosmetic enhancement or effect or a combination of these properties. The term lens includes but is not limited to contact lenses, intraocular lenses, overlay lenses, ocular inserts, punctual plugs, and optical inserts made of materials that can absorb water. Lenses may be made from hydrogels, which include but are not limited to silicone hydrogels, and fluorohydrogels.

For example the term lens includes but is not limited to those made from the soft contact lens formulations described in U.S. Pat. No. 5,710,302, WO 9421698, EP 406161, JP 2000016905, U.S. Pat. No.5,998,498, U.S. patent application Ser. No. 09/532,943, U.S. Pat. Nos. 6,087,415, 5,760,100, 5,776,999, 5,789,461, 5,849,811, and 5,965,631. In addition, metal salts of the invention may be added to commercial soft contact lenses. Examples of soft contact lenses formulations include but are not limited to the formulations of etafilcon A, genfilcon A, lenefilcon A, polymacon, acquafilcon A, balafilcon A, galyfilcon A, senofilcon A and lotrafilcon A. The preferable lens formulations are etafilcon A, balafilcon A, acquafilcon A, galyfilcon A, lotrafilcon A, and silicone hydrogels, as prepared in U.S. Pat. No. 5,998,498, U.S. Ser. No. 09/532,943, a continuation-in-part of U.S. patent application Ser. No. 09/532,943, filed on Aug. 30, 2000, WO03/22321, U.S. Pat. Nos. 6,087,415, 5,760,100, 5,776, 999, 5,789,461, 5,849,811, and 5,965,631. These patents as well as all other patent disclosed in this paragraph are hereby incorporated by reference in their entirety.

Preferably the metal salts are added to lenses made from silicone hydrogel components. A silicone-containing component is one that contains at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone components which may be included in the silicone hydrogel formulations include, but are not limited to silicone macromers, prepolymers and monomers. Examples of silicone macromers include, without limitation, polydimethylsiloxane methacrylated with pendant hydrophilic groups as described in U.S.

Pat. Nos. 4,259,467; 4,260,725 and 4,261,875; polydimethylsiloxane macromers with polymerizable functional group(s) described in U.S. Pat. Nos. 4,136,250; 4,153,641; 4,189,546; 4,182,822; 4,343,927; 4,254,248; 4,355,147; 4,276,402; 4,327,203; 4,341,889; 4,486,577; 4,605,712; 4,543,398; 4,661,575; 4,703,097; 4,837,289; 4,954,586; 4,954,587; 5,346,946; 5,358,995; 5,387,632 ; 5,451,617; 5,486,579; 5,962,548; 5,981,615; 5,981,675; and 6,039,913; polysiloxane macromers incorporating hydrophilic monomers such as those described in U.S. Pat. Nos. 5,010,141; 5,057,578; 5,314,960; 5,371,147 and 5,336,797; macromers comprising polydimethylsiloxane blocks and polyether blocks such as those described in U.S. Pat. Nos. 4,871,785 and 5,034,461, combinations thereof and the like. All of the patents cited herein are hereby incorporated in their entireties by reference.

The silicone and/or fluorine containing macromers described in U.S. Pat. Nos. 5,760,100; 5,776,999; 5,789,461; 5,807,944; 5,965,631 and 5,958,440 may also be used. Suitable silicone monomers include tris(trimethylsiloxy)silylpropyl methacrylate, hydroxyl functional silicone containing monomers, such as 3-methacryloxy-2-hydroxypropyloxy) propylbis(trimethylsiloxy)methylsilane and those disclosed in WO03/22321, and mPDMS containing or the siloxane monomers described in U.S. Pat. Nos. 4,120,570, 4,139,692, 4,463,149, 4,450, 264, 4,525,563; 5,998,498; 3,808,178; 4,139,513; 5,070,215; 5,710,302; 5,714,557 and 5,908,906.

Additional suitable siloxane containing monomers include, amide analogs of TRIS described in U.S. Pat. No. 4,711,943, vinylcarbamate or carbonate analogs described in U.S. Pat. No. 5,070,215, and monomers contained in U.S. Pat. No. 6,020,445, monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof. All of the references mentioned in this application are hereby incorporated by reference in their entirety.

As used herein the term "appropriate time" refers to duration that the solution of step (b) is in contact with the lens after step (a). The preferred appropriate time is about 10 seconds to about 30 seconds, most preferably about 20 seconds.

It has been found that ophthalmic devices produced by the methods of the invention incorporate metal salts with a minimal amount of haze. Preferably, the lenses of the invention are optically clear, with optical clarity comparable to lenses such as lenses made from etafilcon A, genfilcon A, galyfilcon A, lenefilcon A, polymacon, acquafilcon A, balafilcon A, and lotrafilcon A. Specifically, lenses of the present invention have a percent haze that is less than about 100%, preferably less than about 50%, more preferably less than about 25%, even more preferably less than about 20%, even more preferably, between less than about 15%.

The percentage of haze is measured using the following method. A hudrated test lens in borate buffered saline (SSPS) is placed in a clear 20×40×10 mm glass cell at ambient temperature above a flat black background, illuminating from below with a fiber optic lamp (Titan Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

The term "cured" refers to any of a number of methods used to react a mixture of lens components (ie, momoner, prepolymers, macromers and the like) to form lenses. Lenses can be cured by light or heat. The preferred method of curing is with radiation, preferably UV or visible light, and most preferably with visible light. The lens formulations of the present invention can be formed by any of the methods know to those skilled in the art, such as shaking or stirring, and used to form polymeric articles or devices by known methods.

For example, the antimicrobial lenses of the invention may be prepared by mixing reactive components and any diluent(s) with a polymerization initator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the lens formulation in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197, 266. The preferred method for producing antimicrobial lenses of this invention is by molding. In the case of hydrogel lenses, for this method, the lens formulation is placed in a mold having the approximate shape of the final desired lens, and the lens formulation is subjected to conditions whereby the components polymerize, to produce a hardened disc that is subjected to a number of different processing steps including treating the polymerized lens with liquids (such as water, inorganic salts, or organic solutions) to swell, or otherwise equilibrate this lens prior to enclosing the lens in its final packaging. These methods are further described in U.S. Pat. Nos. 4,495,313; 4,680,336; 4,889,664; and 5,039,459, which are hereby incorporated herein by reference. Polymerized lenses that have not been swelled or otherwise equilibrated are considered cured lenses for purposes of this invention.

Additional components may be added to one of more of the steps of the invention. Dispersing agents as described in U.S. patent application Ser. No. 11/924,694, entitled "Processes to Prepare Antimicrobial Contact Lenses," which is hereby incorporated by reference includes examples of such components. The preferred dispersing agents include but are not limited polyvinylpyrrolidone ("PVP"), polyvinylalcohol ("PVA") and derivatives, glycerine, polyethylene oxide ("PEO"), poly(dimethyl acrylamide), poly(N-vinyl-N-methylacetamide), cysteine, methionine, sodium sulfide, sodium thiosulfate, and sodium thiocyanate. The concentration of dispersing agents in the solutions is as disclosed in U.S. patent application Ser. No. 11/924,694. The particularly preferred dispersing agent is PVP, most particularly PVP K90.

An example of the method of the invention follows. Senofilcon A lenses are taken from the manufacturing line after curing and hydration with deionized water. The lenses are soaked in an aqueous solution containing sodium iodide (1000 ppm) and a 50% aqueous isopropanol solution. The lenses remain in the afore-mentioned solutions for about 20 minutes at 25° C. and are cooled to 0° C. for another 20 minutes. The lenses are removed from the solution and rinsed with a solution of 50% aqueous isopropanol for about 20 to 30 seconds. The lenses are removed from said solution and placed in a solution of 50% aqueous isopropanol and 5% aqueous silver nitrate for about five minutes. The lenses are removed from these solutions and are rinsed with borate buffered packaging solution (1.4% % sodium sulfate with 30 ppm of methyl cellulose pH 7.3). These lenses contain between 15 and 20 µg of silver and a haze value of about 20%.

Further, the invention includes an antimicrobial lens comprising, a metal salt, made by a method comprise the steps of
(a) treating a cured lens, with a solution comprising salt precursor and a swelling agent,
(b) treating the lens of step (a) with solution comprising a swelling agent for an appropriate time, and
(c) treating the lens of step (b) with a solution comprising a metal agent and a swelling agent.

The terms antimicrobial lens, metal salt, salt precursor, metal agent, swelling agent solution, appropriate time, and treating all have their aforementioned meanings and preferred ranges.

The aforementioned methods and devices of the invention are meant to illustrate the invention and suggest methods and devices that embody the invention. Those knowledgeable in contact lenses as well as other specialties may find other methods of practicing the invention. However, those methods are deemed to be within the scope of this invention.

What is claimed is:

1. A method of preparing an antimicrobial lens comprising a metal salt, wherein said method comprises the steps of
   (a) treating a cured lens, with a solution comprising salt precursor and a swelling agent,
   (b) treating the lens of step (a) after removing it from the solution of step (a) with a solution comprising a swelling agent for an appropriate period of time of about 10 to about 30 seconds, and
   (c) treating the lens of step (b) after removing it from the solution of step (b) with a solution comprising a metal agent and a swelling agent wherein the swelling agents used in each step can be the same or different from the swelling agent used in each other step.

2. The method of claim 1 wherein at least one of the swelling agents is selected from the group consisting of ethylene glycol-n-butyl ether, diethylene glycol-n-butyl ether, diethylene glycol methyl ether, ethylene glycol phenyl ether, propylene glycol methyl ether, dipropylene glycol methyl ether, tripropylene glycol methyl ether, propylene glycol methyl ether acetate, dipropylene glycol methyl ether acetate, propylene glycol-n-propyl ether, dipropylene glycol-n-propyl ether, tripropylene glycol-n-butyl ether, propylene glycol-n-butyl ether, dipropylene glycol-n-butyl ether, tripropylene glycol-n-butyl ether, tripropylene glycol-n-propyl ether, proplyene glycol phenyl ether, dipropylene glycol dimethyl ether, butyl acetate, dipropylene glycol methyl ether acetate, and dipropylene dimethyl ether.

3. The method of claim 1 wherein at least one of the swelling agents is aqueous isopropanol, or aqueous propylene glycol.

4. The method of claim 1 wherein at least one of the swelling agents is about 30% to about 70% aqueous isopropanol.

5. The method of claim 1 wherein at least one of the swelling agents is 50% aqueous isopropanol.

6. The method of claim 1 wherein at least one of the swelling agents is aqueous propylene glycol.

7. The method of claim 1 wherein the salt precursor is selected from the group consisting sodium chloride, sodium iodide, sodium bromide, sodium sulfide, lithium chloride, lithium iodide, lithium bromide, lithium sulfide, potassium bromide, potassium chloride, potassium sulfide, potassium iodide, rubidium iodide, rubidium bromide, rubidium chloride, rubidium sulfide, caesium iodide, caesium bromide, caesium chloride, caesium sulfide, francium iodide, francium bromide, francium chloride, francium sulfide, and sodium tetrachloro argentate.

8. The method of claim 1 wherein the salt precursor is sodium iodide.

9. The method of claim 1 wherein the metal agent is selected from the group consisting of silver nitrate, silver triflate, or silver acetate, silver sulfate, silver tetrafluoroborate, silver sulfate, zinc acetate, zinc sulfate, copper acetate, and copper sulfate.

10. The method of claim 1 wherein the metal agent is silver nitrate.

11. The method of claim 1 wherein the appropriate time is about 10 to about 20 seconds.

12. The method of claim 1 wherein the appropriate time is about 20 to about 30 seconds.

13. The method of claim 1 wherein one or more of the solutions of steps (a), (b), and (c) comprise a dispersing agent.

14. The method of claim 13, wherein the dispersing agent is selected from the group consisting of polyvinylpyrrolidone, polyvinylalcohol and derivatives, glycerine, polyethylene oxide, poly(dimethyl acrylamide), poly(N-vinyl-N-methylacetamide), cysteine, methionine, sodium sulfide, sodium thiosulfate, and sodium thiocyanate.

15. The method of claim 13 wherein the dispersing agent is polyvinylpyrrolidone K90.

* * * * *